(12) United States Patent
Sato et al.

(10) Patent No.: US 8,496,576 B2
(45) Date of Patent: Jul. 30, 2013

(54) IN-VIVO INFORMATION ACQUIRING SYSTEM AND METHOD FOR CONTROLLING IN-VIVO INFORMATION ACQUIRING SYSTEM

(75) Inventors: Ken Sato, Nagano (JP); Fukashi Yoshizawa, Ina (JP)

(73) Assignee: Olympus Corporation, Tokyo (JP)

( * ) Notice: Subject to any disclaimer, the term of this patent is extended or adjusted under 35 U.S.C. 154(b) by 579 days.

(21) Appl. No.: 12/748,828

(22) Filed: Mar. 29, 2010

(65) Prior Publication Data

US 2010/0249508 A1      Sep. 30, 2010

(30) Foreign Application Priority Data

Mar. 31, 2009  (JP) ................................. 2009-086699

(51) Int. Cl.
*A61B 1/04*       (2006.01)

(52) U.S. Cl.
USPC ......................................................... 600/117

(58) Field of Classification Search
USPC ........................................................ 600/117
See application file for complete search history.

(56) References Cited

U.S. PATENT DOCUMENTS

| | | | |
|---|---|---|---|
| 7,118,531 B2 * | 10/2006 | Krill | 600/309 |
| 7,922,653 B2 * | 4/2011 | Homan | 600/118 |
| 2004/0225185 A1 * | 11/2004 | Obata et al. | 600/118 |
| 2009/0076326 A1 * | 3/2009 | Mitsuhashi et al. | 600/118 |
| 2009/0163771 A1 * | 6/2009 | Kimoto et al. | 600/118 |
| 2011/0124983 A1 * | 5/2011 | Kroll et al. | 600/302 |

FOREIGN PATENT DOCUMENTS

JP        2005-237460        9/2005

* cited by examiner

*Primary Examiner* — Rodney Fuller
(74) *Attorney, Agent, or Firm* — Scully, Scott, Murphy & Presser, P.C.

(57) ABSTRACT

A capsule endoscope system provided with a magnetic field generating apparatus including an input section for inputting identification information A and a magnetic field generating section that generates a magnetic field signal that controls a capsule endoscope, and the capsule endoscope including an in-vivo information acquiring section, a battery, a magnetic field receiving section, a storage section that stores identification information B, a control section and a comparing section that compares the identification information A with the identification information B and judges whether both pieces of information are the same or different, wherein when the judgment by the comparing section is a judgment that both pieces of information are the same, the control section supplies or shuts off power from the battery to the in-vivo information acquiring section.

16 Claims, 11 Drawing Sheets

IN-VIVO INFORMATION ACQUIRING SYSTEM AND METHOD FOR CONTROLLING IN-VIVO INFORMATION ACQUIRING SYSTEM

This application claims the benefit of Japanese Application No. 2009-086699 filed in Japan on Mar. 31, 2009, the contents of which are incorporated herein by this reference.

BACKGROUND OF THE INVENTION

1. Field of the Invention

The present invention relates to an in-vivo information acquiring system provided with an in-vivo information acquiring apparatus introduced into an object to be examined and an external signal generating apparatus disposed outside the in-vivo information acquiring apparatus that operates the in-vivo information acquiring apparatus, and a method for controlling the in-vivo information acquiring system.

2. Description of the Related Art

In recent years, swallow type capsule endoscopes are making their debuts in the field of endoscopes. A capsule endoscope is introduced into a body by being swallowed from an examinee's mouth and moves inside a body cavity, for example, organs such as stomach and small intestine according to peristaltic movement and picks up images one by one until the capsule endoscope is spontaneously discharged.

Image data picked up in the body by the capsule endoscope while the capsule endoscope moves through the body cavity are transmitted one by one to the outside through wireless communication and stored in a memory provided in an outside receiver. By carrying the receiver, a patient can freely act after swallowing the capsule endoscope until the capsule endoscope is discharged.

The capsule endoscope obtains drive power from a battery or the like, which is built in a casing, but since the capsule endoscope has a structure with an inner circuit or the like hermetically sealed in the casing, a user cannot perform ON/OFF operation to drive the endoscope by operating a switch or the like disposed on the outer surface of the casing. Thus, an in-vivo observation system is proposed which is provided with a reed switch short-circuited/released by an outside magnetic field in the casing of a capsule endoscope.

For example, in a capsule endoscope 110 of an in-vivo observation system 101 disclosed by the present applicant in Japanese Patent Application Laid-Open Publication No. 2005-237460 shown in FIG. 1, power is distributed to a plurality of circuits by a DC magnetic field generated by coils 144 and 145 driven by current drivers 146 and 147 of an outside magnetic field generating apparatus 120 at optimum timing respectively.

That is, as shown in FIG. 2, by applying a magnetic field from the outside magnetic field generating apparatus 120 to a reed switch 126a of the capsule endoscope 110 a plurality of times and thereby causing an FET 126d, which is a main switch, and an FET 126e, which is an RF switch, to perform ON/OFF operation one by one, it is possible to distribute power to an LED drive circuit 121 that drives an LED 127, a CCD drive circuit 123 that drives a CCD 122 and an RF transmission unit 124 at optimum timing respectively. In FIG. 2, flip flops 126b and 126c constitute a latch circuit for a toggle operation.

In the capsule endoscope 110, the reed switch 126a turns ON/OFF by a magnetic field generated by the coils 144 and 145 and the FET 126d thereby controls a power supply from a battery 129 through the toggle operation.

Here, when the capsule endoscope is administered to a plurality of examinees, a plurality of capsule endoscopes of the same type or different types are prepared for the respective examinees. Activation/stopping of the respective capsule endoscopes needs to be controlled as appropriate.

BRIEF SUMMARY OF THE INVENTION

In order to attain the above described object, an in-vivo information acquiring system according to an embodiment of the present invention is provided with a magnetic field generating apparatus including an input section for inputting first identification information that allows an in-vivo information acquiring apparatus to be controlled to be distinguished from other in-vivo information acquiring apparatuses and a magnetic field generating section that generates a magnetic field signal that controls the in-vivo information acquiring apparatus to be controlled, and an in-vivo information acquiring apparatus introduced into an object to be examined and to be controlled including an in-vivo information acquiring section that acquires information inside the object to be examined, a power supply source that supplies power to be used to drive the in-vivo information acquiring section, a magnetic field signal receiving section disposed outside that receives the magnetic field signal from the external signal generating apparatus, a storage section that stores second identification information that allows the in-vivo information acquiring apparatus to be controlled to be distinguished from the other in-vivo information acquiring apparatuses and a power supply control section that controls a power supply from the power supply source to the in-vivo information acquiring section.

However, when the in-vivo information acquiring system has any one of configurations where (1) the magnetic field generating apparatus includes a first comparing section that compares the first identification information with the second identification information and judges whether both pieces of information are the same or different, (2) the in-vivo information acquiring apparatus to be controlled includes a second comparing section that compares the first identification information with the second identification information and judges whether both pieces of information are the same or different and (3) the magnetic field generating apparatus includes the first comparing section and the in-vivo information acquiring apparatus to be controlled includes the second comparing section, and when the judgment of at least one of the first comparing section and the second comparing section is a judgment that both pieces of information are the same, the power supply control section supplies or shuts off power from the power supply source to the in-vivo information acquiring section.

Furthermore, a method for controlling an in-vivo information acquiring system according to another embodiment of the present invention includes a first identification information inputting step of inputting first identification information that allows an in-vivo information acquiring apparatus to be controlled to be distinguished from other in-vivo information acquiring apparatuses from an input section of a magnetic field generating apparatus that generates a magnetic field signal for controlling the in-vivo information acquiring apparatus to be controlled and is disposed outside the in-vivo information acquiring apparatus to be controlled, a magnetic field generating step of generating a magnetic field signal of an instruction signal from a magnetic field generating section of the magnetic field generating apparatus to the in-vivo information acquiring apparatus to be controlled and a magnetic field signal of the first identification information, a magnetic field signal receiving step of a magnetic field signal receiving section of the in-vivo information acquiring apparatus to be controlled receiving a magnetic field signal from the external signal generating apparatus, a comparing step of a comparing section of the in-vivo information acquiring apparatus to be controlled comparing second identification information stored in a storage section of the in-vivo information acquiring apparatus to be controlled that allows the in-vivo information acquiring apparatus to be controlled to be distinguished from other in-vivo information acquiring apparatuses with the first identification information received from the external signal generating apparatus and judging whether both pieces of information are the same or different, and a power supply controlling step of a power supply control section controlling whether power from a power supply source to an in-vivo information acquiring section is supplied or shut off when the judgment by the comparing section is a judgment that both pieces of information are the same.

Furthermore, a method for controlling an in-vivo information acquiring system according to a further embodiment of the present invention includes a first identification information inputting step of inputting first identification information that allows an in-vivo information acquiring apparatus to be controlled to be distinguished from other in-vivo information acquiring apparatuses from an input section of a magnetic field generating apparatus that generates a magnetic field signal for controlling the in-vivo information acquiring apparatus to be controlled and is disposed outside the in-vivo information acquiring apparatus to be controlled, an identification information magnetic field generating step of generating a magnetic field signal of the first identification information from a magnetic field generating section of the magnetic field generating apparatus, a magnetic field signal receiving step of a magnetic field signal receiving section of the in-vivo information acquiring apparatus to be controlled receiving a magnetic field signal of the first identification information from the external signal generating apparatus, a second identification information transmitting step of a wireless transmitting section of the in-vivo information acquiring apparatus to be controlled wirelessly transmitting second identification information stored in a storage section of the in-vivo information acquiring apparatus to be controlled that allows the in-vivo information acquiring apparatus to be controlled to be distinguished from other in-vivo information acquiring apparatuses, a second identification information receiving step of a wireless receiving section of the magnetic field generating apparatus receiving second identification information from the in-vivo information acquiring apparatus to be controlled, a comparing step of a comparing section of the magnetic field generating apparatus comparing the first identification information inputted in the first identification information inputting step with the second identification information received in the second identification information receiving step and judging whether both pieces of information are the same or different, an instruction magnetic field signal transmitting step of transmitting a magnetic field signal of an instruction signal for the in-vivo information acquiring apparatus to be controlled from the magnetic field generating section based on the judgment by the comparing section, a magnetic field signal receiving step of a magnetic field signal receiving section of the in-vivo information acquiring apparatus to be controlled receiving the magnetic field signal of the instruction signal from the external signal generating apparatus, and a power supply controlling step of a power supply control section controlling whether power from a power supply source to an in-vivo information acquiring section is supplied or shut off based on the instruction signal.

DETAILED DESCRIPTION OF THE PREFERRED EMBODIMENTS

First Embodiment

Figure 3:
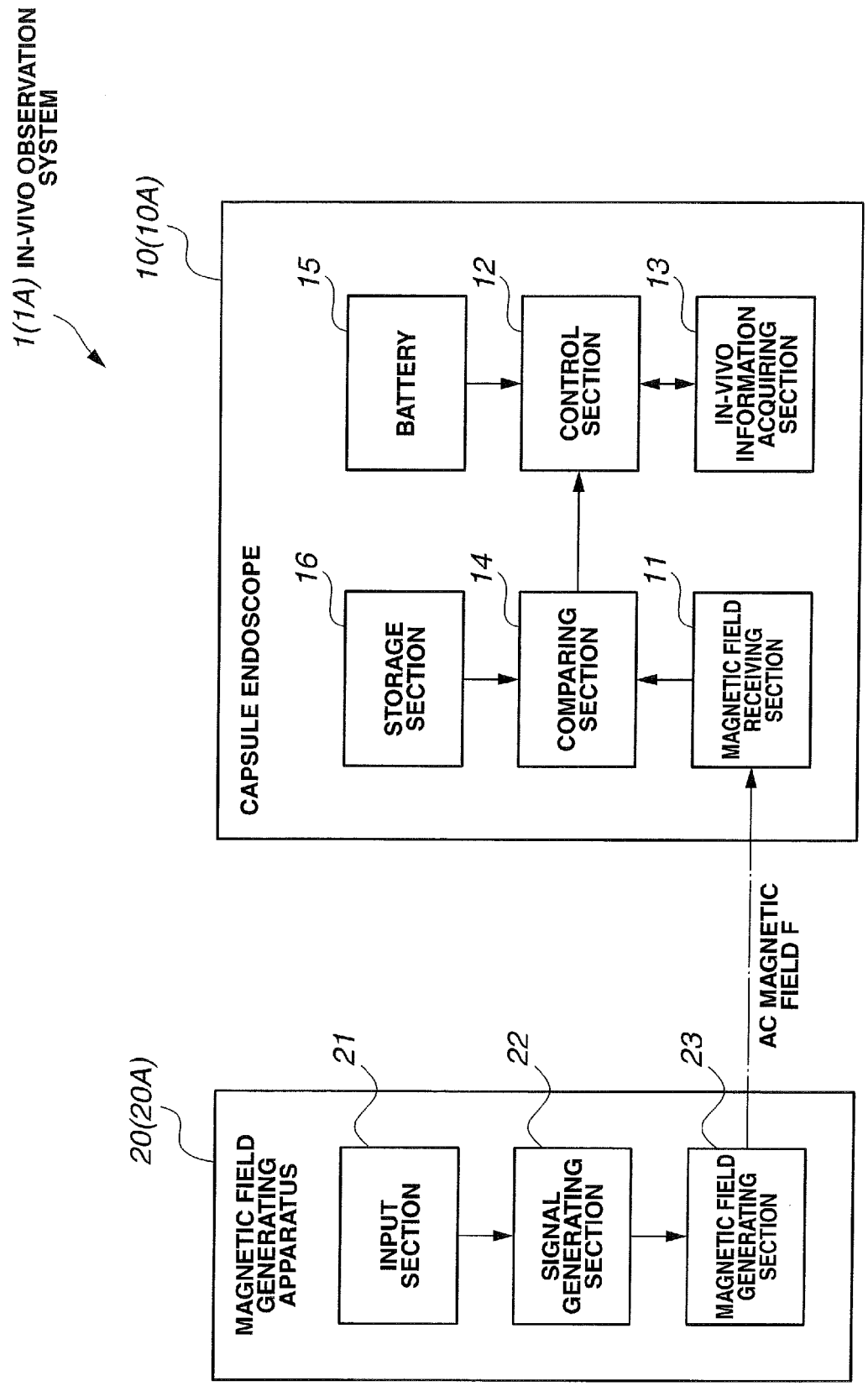
FIG. 3 is a block diagram illustrating a configuration of an in-vivo observation system according to a first embodiment.
Figure 4:
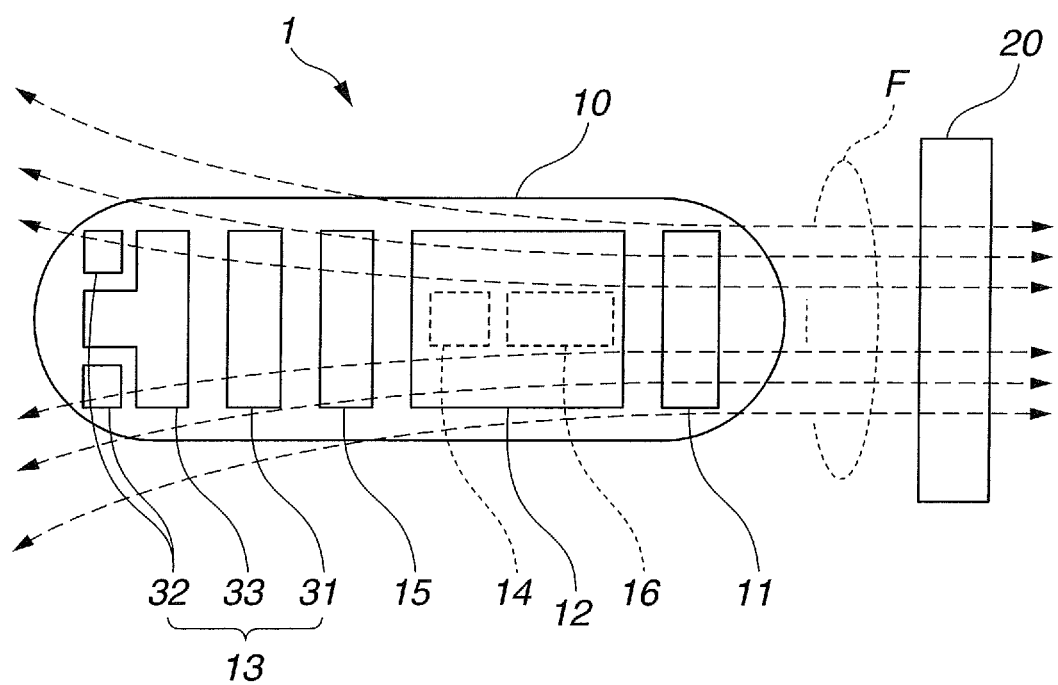
FIG. 4 is a schematic view schematically illustrating the configuration of the in-vivo observation system of the first embodiment.

An in-vivo observation system 1, which is an in-vivo information acquiring system according to a first embodiment of the present invention will be described using FIG. 3 to FIG. 6. As shown in FIG. 3 and FIG. 4, the in-vivo observation system 1 of the present embodiment includes a capsule endoscope 10, which is an in-vivo information acquiring apparatus to be controlled introduced into an object to be examined and a magnetic field generating apparatus 20 disposed outside the capsule endoscope 10 that generates an AC magnetic field signal (hereinafter also simply referred to as "magnetic field" or "magnetic field signal") that controls the capsule endoscope 10 to be controlled.

The magnetic field generating apparatus 20 has an input section 21, a signal generating section 22 and a magnetic field generating section 23. A user inputs identification information A, which is first identification information that allows a predetermined capsule endoscope 10 to be controlled to be activated or stopped under the control of the magnetic field generating apparatus 20 using the input section 21 to be distinguished from other capsule endoscopes, which are different from the capsule endoscope 10. The signal generating section 22 generates a signal regarding a frequency, a phase or a magnetic field strength or the like of an AC magnetic field generated by the magnetic field generating section 23 based on the identification information A. The magnetic field generating section 23 generates the AC magnetic field signal based on the signal generated by the signal generating section 22.

The capsule endoscope 10 includes an in-vivo information acquiring section 13, which is a main function section, a magnetic field receiving section 11, a comparing section 14, a storage section 16, a battery 15 and a control section 12. The magnetic field receiving section 11 is a magnetic field signal receiving section that receives the AC magnetic field from the magnetic field generating apparatus 20. The storage section 16 stores identification information B, which is information that allows the capsule endoscope 10 to be distinguished from other in-vivo observation apparatuses, that is, second identification information specific to the capsule endoscope 10. The comparing section 14, which is a second comparing section, is an identification information comparing section that compares the identification information A received by the magnetic field receiving section 11 with the identification information B and judges whether both pieces of information are the same or different, in other words, judges the difference between both pieces of information. The battery 15 is a power supply source that supplies power used to drive the in-vivo information acquiring section 13. The control section 12 is a power supply control section that controls power from the battery 15 to the in-vivo information acquiring section 13 according to the magnetic field signal received by the magnetic field receiving section 11 and the judgment result of the comparing section 14 and also controls the entire capsule endoscope 10.

As shown in FIG. 4, in the in-vivo observation system 1, the AC magnetic field F generated by the magnetic field generating apparatus 20 is preferably applied parallel to the longitudinal direction of the capsule endoscope 10. This is because the magnetic path, which is a magnetic field detecting measure of the magnetic field receiving section 11 is parallel to the longitudinal direction of the capsule endoscope 10.

Figure 5:
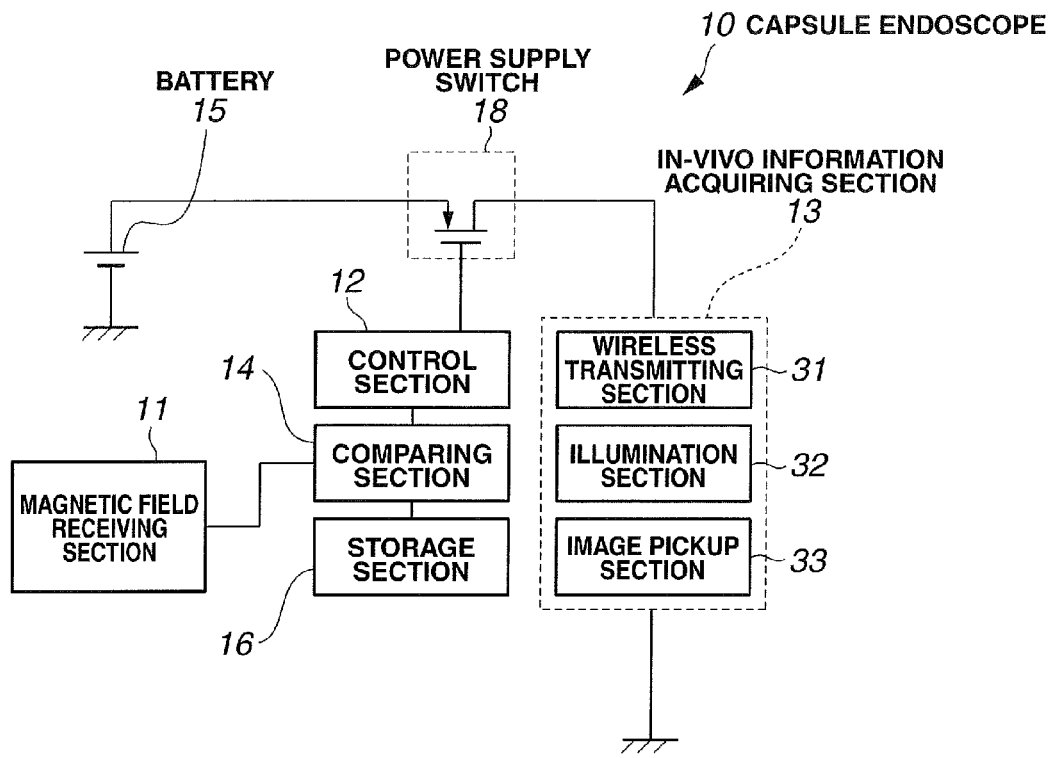
FIG. 5 is a block diagram illustrating a configuration of a capsule endoscope of the first embodiment.

Next, the configuration of the capsule endoscope 10 will be described using FIG. 5. As shown in FIG. 5, the in-vivo information acquiring section 13 is the main function section of the capsule endoscope 10 that observes in-vivo information and wirelessly transmits the observed information. The in-vivo information acquiring section 13 includes an illumination section 32, an image pickup section 33 and a wireless transmitting section 31. The illumination section 32 includes, for example, an LED that irradiates the wall surface of an organ in the body with light. The image pickup section 33 includes a solid image pickup device such as a CCD or a CMOS image sensor that picks up an image of the wall surface of an organ in the body. The wireless transmitting section 31 is a video information wireless transmitting section including a transmitting circuit and a transmitting antenna to wirelessly transmit video information obtained by the image pickup section 33 to the outside of the body. The video information transmitted by the wireless transmitting section 31 is stored in a memory provided in an outside receiver.

As has already been described, the storage section 16 stores identification information B, that is, specific information that allows the predetermined capsule endoscope 10 controlled to be distinguished from other capsule endoscopes which are different from the capsule endoscope 10, in other words, information that can specify the respective capsule endoscopes 10. That is, although the capsule endoscope 10 to be controlled and other capsule endoscopes not to be controlled have the same specification, but are different from each other in identification information. The identification information B is, more specifically, a model, a manufacturing number, information on the user or a name of the facility used or the like or a combination thereof. The timing at which the identification information B is stored in the storage section 16 is, for example, the time of manufacturing or when used by the user such as a medical doctor or a nurse.

Though details are not illustrated, the magnetic field receiving section 11 includes a receiving antenna that receives an AC magnetic field, a diode that rectifies the AC signal received by the receiving antenna, a smoothing capacitor that smoothes the AC signal and a resistor that discharges the electric charge charged in the smoothing capacitor. That is, the magnetic field receiving section 11 converts the AC magnetic field signal received to a DC current signal. The receiving antenna is a resonance circuit including a secondary side coil and a secondary side capacitor, and is adjusted so as to resonate with the frequency of the AC magnetic field from the magnetic field generating apparatus 20. Therefore, the capsule endoscope 10 can perform stable control free of erroneous activation or erroneous stopping. That is, detecting sensitivity for the AC magnetic field applied from the magnetic field generating apparatus 20 is improved and activation and stopping of the capsule endoscope 10 is easily controllable. On the other hand, since the frequency of an unintended disturbance magnetic field is not a resonance frequency, detecting sensitivity is low and the capsule endoscope 10 is never activated or stopped by the disturbance magnetic field.

A power supply switch 18 is a power switch made up of a P-channel type FET that controls ON/OFF of a power supply from the battery 15 to the in-vivo information acquiring section 13. That is, the drain of the power supply switch 18 is connected to the battery 15, the gate is connected to the output of the control section 12 and the source is connected to each circuit of the in-vivo information acquiring section 13. The control section 12 controls the power supply switch 18 based on the information on the AC magnetic field signal received from the magnetic field receiving section 11 and the judgment of the comparing section 14. The power supply switch 18 preferably performs a toggle operation.

Figure 1:
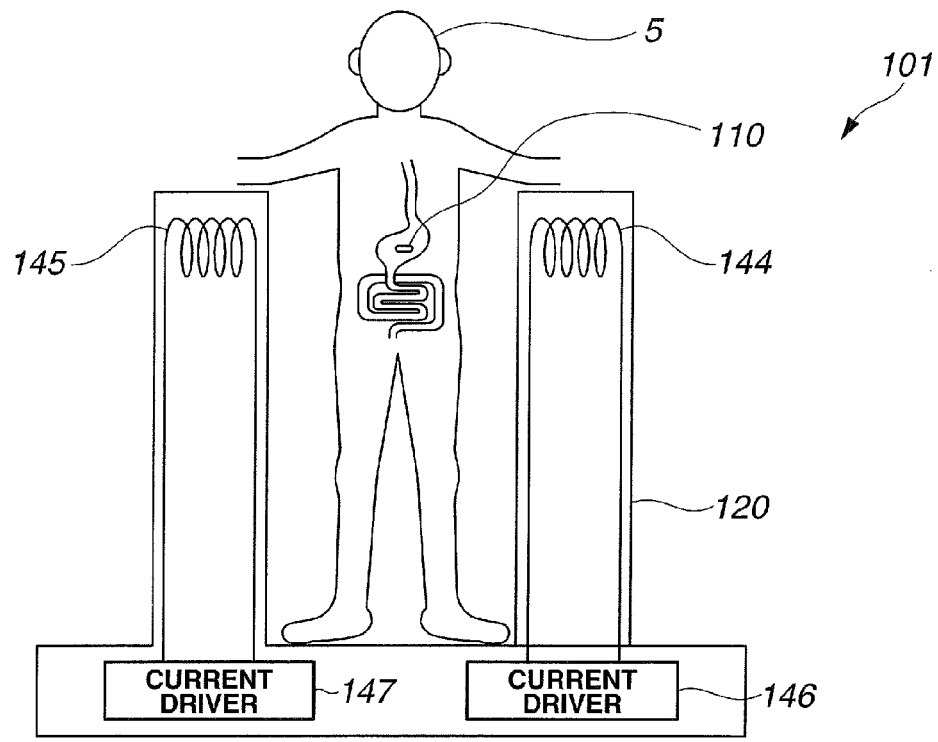
FIG. 1 is a schematic view illustrating a publicly known in-vivo observation system.
Figure 2:
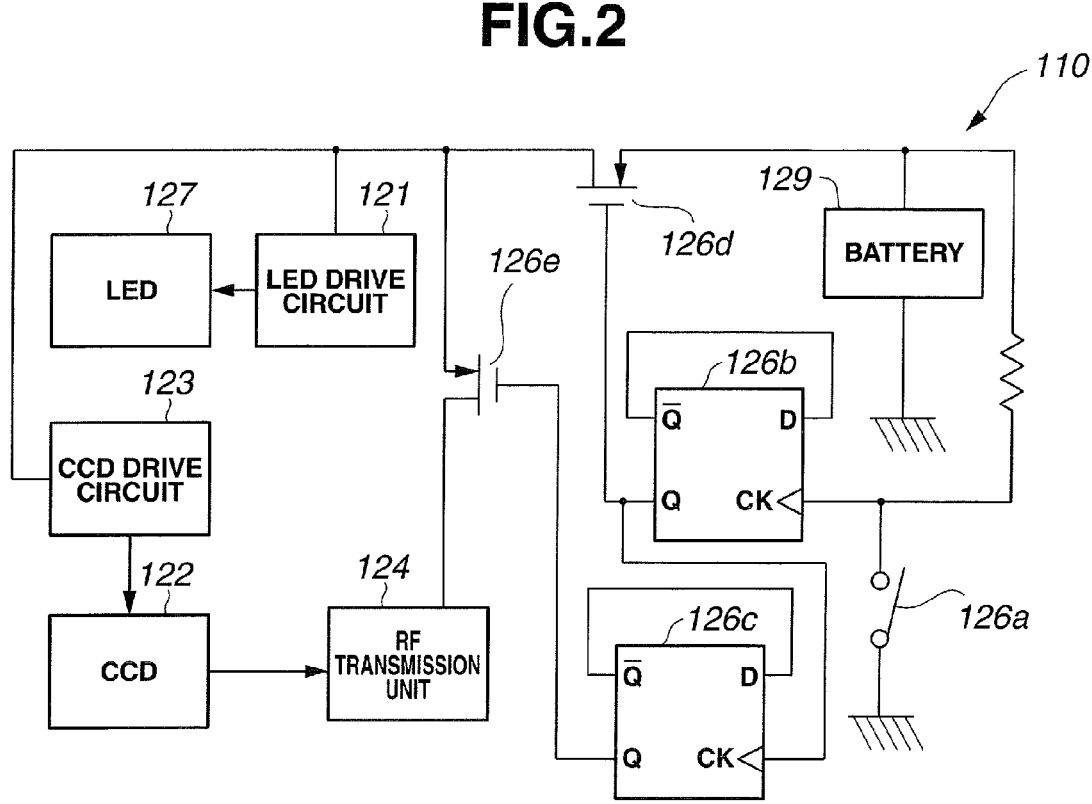
FIG. 2 is a block diagram illustrating a configuration of a capsule endoscope of the publicly known in-vivo observation system.
Figure 6:
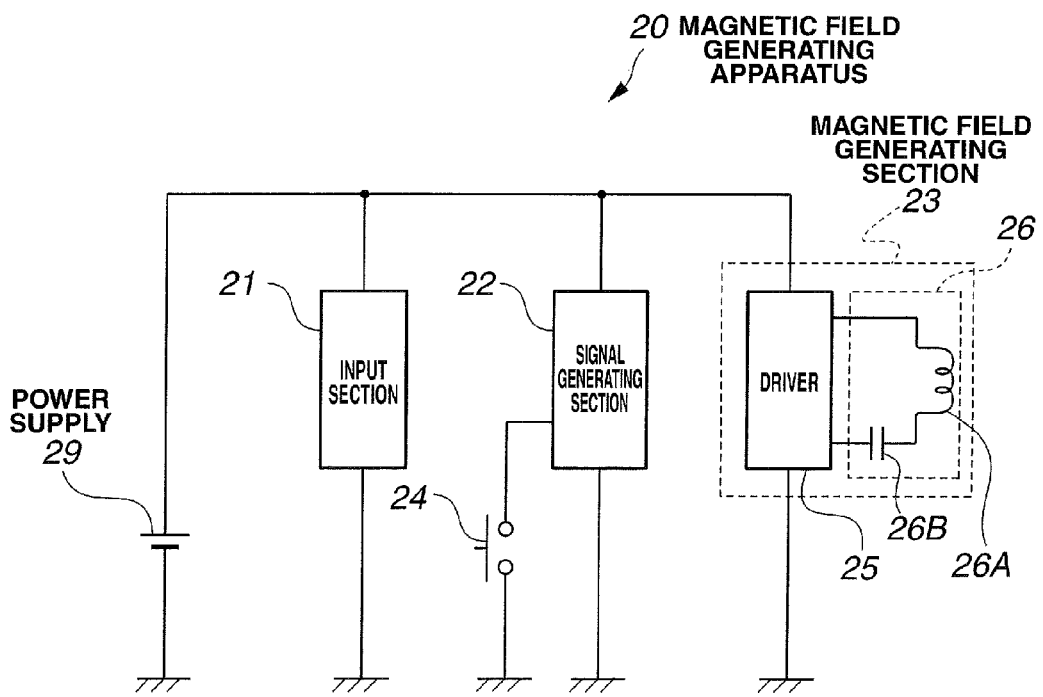
FIG. 6 is a block diagram illustrating a configuration of a magnetic field generating apparatus of the first embodiment.

Next, the configuration of the magnetic field generating apparatus 20 will be further described using FIG. 6. Unlike a large magnetic field generating apparatus 120 as shown in FIG. 1, the magnetic field generating apparatus 20 of the present embodiment is, for example, a magnetic field generating apparatus for activating the capsule endoscope 10 before swallowing and is a small power supply starter in an approximately palm size. However, since the magnetic field generating apparatus 20 uses the AC magnetic field as a magnetic field signal, unlike the magnetic field generating apparatus 120 that uses the DC magnetic field as shown in FIG. 1, the magnetic field generating apparatus 20 need not generate a very strong magnetic field. Therefore, the magnetic field generating apparatus 20 can not only activate and stop the capsule endoscope 10 outside the body but also control activation and stopping of the capsule endoscope 10 in the body.

As shown in FIG. 6, the magnetic field generating section 23 has a primary side coil 26A and a primary side capacitor 26B that make up a resonance circuit 26 and a driver 25, and generates an AC magnetic field signal. The driver 25 generates a current to drive the primary side coil 26A, which is a transmitting antenna, based on the signal generated by the signal generating section 22.

A stabilization power supply, a primary battery, a secondary battery, a solar battery or a fuel battery or the like can be used for a power supply 29 if such a power supply can supply power necessary to generate the AC magnetic field. In the case of the magnetic field generating apparatus 20 connected to another outside apparatus such as a workstation, power may be supplied from the outside apparatus. The input section 21 is, for example, a key pad whereby the identification information A is inputted. The identification information A to be transmitted is displayed beforehand on a case in which the capsule endoscope 10 is stored and the user inputs the identification information A displayed on the case using the input section 21. A switch 24 is a switch for the user to instruct generation of the AC magnetic field.

The transmission coil of the magnetic field generating section 23 and the reception coil of the magnetic field receiving section 11 may be a solenoid type coil or plane coil and no restriction is imposed on the shape thereof.

For simplicity of explanation, the respective components are assumed to be independent components, but the components may be physically parts of other components. For example, the storage section 16 or the comparing section 14 may be made up of the same CPU as that of the control section 12.

Figure 7:
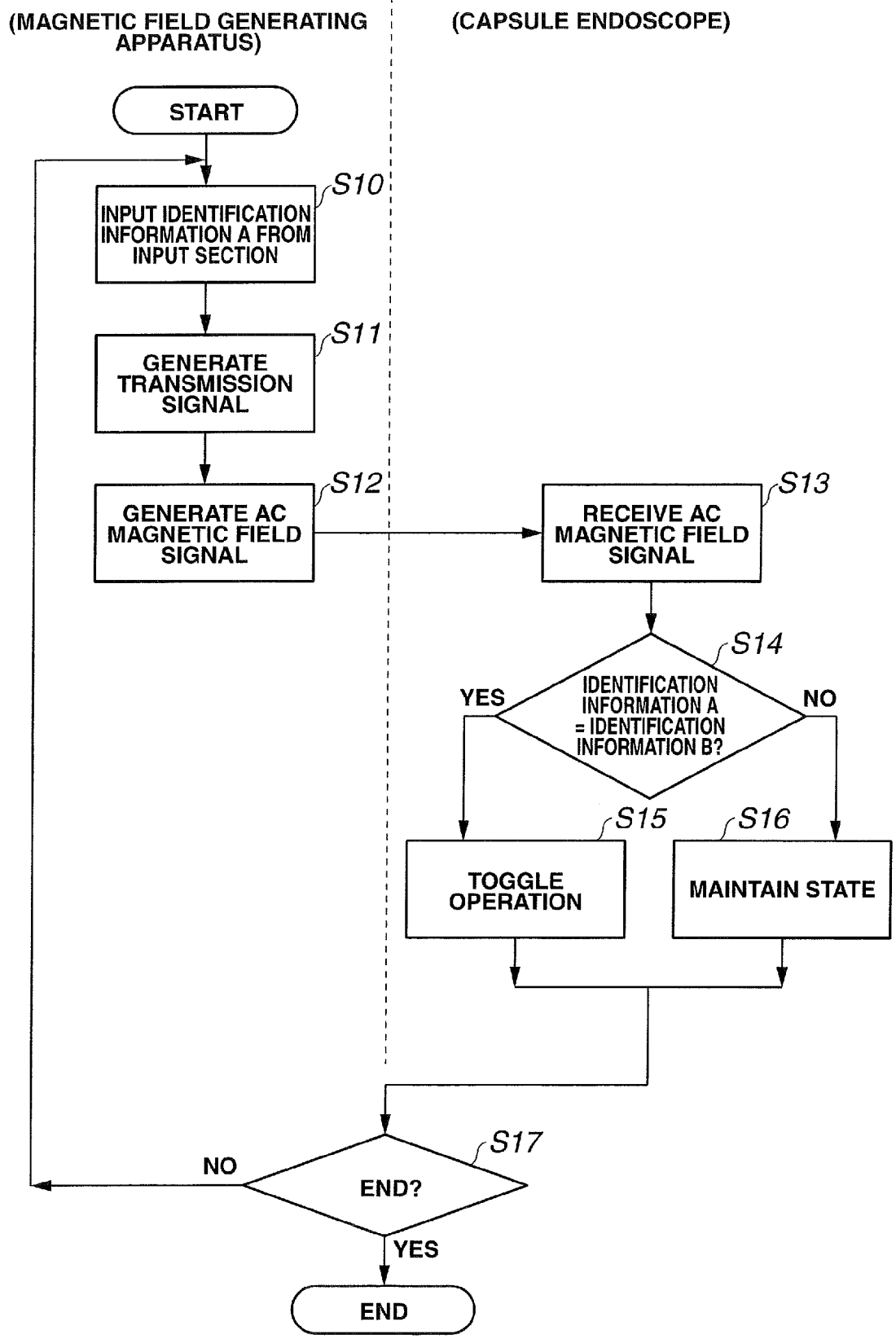
FIG. 7 is a flowchart illustrating a processing flow of the in-vivo observation system of the first embodiment.

Next, a processing flow of the in-vivo observation system 1 of the present embodiment will be described using FIG. 7. Hereinafter, the processing flow of the in-vivo observation system will be described according to the flowchart in FIG. 7. The right side in FIG. 7 shows processing by the capsule endoscope 10 and the left side shows processing by the magnetic field generating apparatus 20.

<Step S10> Input of Identification Information A

At the start, the in-vivo information acquiring section 13 of the capsule endoscope 10 is in a stopped or operating state. The user inputs identification information A, which is first identification information to allow a predetermined capsule endoscope 10 to be controlled to be distinguished from other in-vivo observation apparatuses using the input section 21 of the magnetic field generating apparatus 20.

<Step S11> Generation of Transmission Signal

The signal generating section 22 generates a signal to be transmitted to the driver 25 based on the inputted identification information A.

<Step S12> Generation of AC Magnetic Field Signal

When the user operates the switch 24 of the magnetic field generating apparatus 20, the magnetic field generating section 23 generates an AC magnetic field signal F made up of an instruction signal for activating or stopping the in-vivo information acquiring section 13 of the capsule endoscope 10 and the identification information A. In the in-vivo observation system 1 of the present embodiment, an activation instruction signal and a stop instruction signal are the same signal.

Furthermore, the identification information A to be transmitted may be transmitted superimposed on the activation instruction signal or the stop instruction signal or transmitted in series, that is, separated in time sequence.

Transmitting superimposed signals allows transmission to be completed in a short time, and can thereby shorten the transmission time. Transmitting signals separated in time sequence simplifies transmission/reception processing.

<Step S13> Reception of AC Magnetic Field Signal

The magnetic field receiving section 11 of the capsule endoscope 10 receives the AC magnetic field F from the magnetic field generating apparatus 20. That is, the magnetic field receiving section 11 acquires the identification information A included in the AC magnetic field F simultaneously with conversion of the received AC magnetic field F to a DC current.

<Step S14> Comparison and Judgment of Identification Information

The control section 12 reads the identification information B stored in the storage section 16 and the comparing section 14 compares the identification information A included in the received AC magnetic field F with the read identification information B and judges whether both pieces of information are the same or different. The capsule endoscope 10 performs processing in step S15 when the judgment result shows that both pieces of information are the same (Yes) and performs processing in step S16 when the judgment result shows that both pieces of information are different (No).

<Step S15> Toggle Operation

The control section 12 changes the potential of the gate of the power supply switch 18 and performs an inversion between a high impedance state and a conduction state. That is, when the power supply switch 18 is in a high impedance state, the control section 12 changes the state to a conduction state, and therefore the in-vivo information acquiring section 13 is placed in an operating state. On the other hand, when the power supply switch 18 is in a conduction state, the control section 12 changes the state to a high impedance state and the in-vivo information acquiring section 13 is placed in a stopped state. That is, the power supply switch 18 performs a toggle operation.

<Step S16> Maintenance of State

The control section 12 does not change the potential of the gate of the power supply switch 18, and therefore the state of the in-vivo information acquiring section 13, that is, the operating state or stopped state is maintained.

<Step S17> Continuation of Processing

Until an end instruction is received from the user, the in-vivo observation system 1 repeatedly executes the processing from step S10.

As described above, according to the in-vivo observation system 1 or the method for driving an in-vivo observation system according to the present embodiment, even if a plurality of capsule endoscopes are located inside or outside the body, it is possible to perform non-contact control over activation/stopping of only a predetermined capsule endoscope 10, that is, the in-vivo information acquiring section 13, which is the main function section of the capsule endoscope 10 subject to activation control or stopping control.

That is, even if a plurality of capsule endoscopes exist in proximate locations, there is no possibility that misoperation may occur.

Furthermore, when an abnormality of the capsule endoscope is revealed after an examinee has swallowed the capsule endoscope, a new capsule endoscope of the same type is prepared and administered to the examinee. This means that two capsule endoscopes of the same type exist in the body of the examinee. Even in this case, if a magnetic field is applied to operate the capsule endoscope from outside the body, the two capsule endoscopes are never activated/stopped simultaneously.

Furthermore, to observe different regions of one examinee, different types of capsule endoscopes suitable for the respective regions to be observed may be administered. Even in this case, if a magnetic field is applied to operate the capsule endoscope from outside the body, the plurality of capsule endoscopes are never activated/stopped simultaneously.

That is, according to the in-vivo observation system and the method of driving an in-vivo observation system, even if there are a plurality of in-vivo observation apparatuses, it is possible to exercise control over activation/stopping of only a desired in-vivo observation apparatus.

An accommodation section capable of accommodating the capsule endoscope 10 may be provided in the magnetic field generating apparatus 20 and covered with a cover so as to prevent the capsule endoscope 10 from being taken out until the reception of the identification information B is completed. In this case, the capsule endoscope 10 can reliably receive the identification information B and the reliability of the in-vivo observation system 1 improves.

Furthermore, when a plurality of capsule endoscopes of the same type having the same function are not assumed to be used in proximity to each other, only models may be used as the identification information A and the identification information B. In this case, the number of digits of the identification information compared by the comparing section 14, that is, the amount of information is small and the circuit size of the comparing section 14 can be reduced.

Furthermore, the identification information A to be transmitted by the magnetic field generating apparatus 20 may be displayed beforehand, for example, on a package in which the capsule endoscope 10 is packed with a character string, a barcode or a two-dimensional code or the like. The magnetic field generating apparatus 20 is then provided with an identification information reader to read the identification information A displayed on the package in which the capsule endoscope 10 is packed. The user can read and input the identification information A displayed on the package using the identification information reader which is the input section of the magnetic field generating apparatus 20. In this case, it is possible to prevent erroneous activation or erroneous stopping of the capsule endoscope 10 due to erroneous input of the identification information A.

Furthermore, the case in which the capsule endoscope 10 is stored may be provided with an ID tag that stores the identification information A beforehand. The magnetic field generating apparatus 20 may be provided with an ID tag reader, which is an input section to read the identification information A in the ID tag. The user reads and inputs the identification information A in the ID tag. It is possible to prevent erroneous activation or erroneous stopping of the capsule endoscope 10 due to erroneous input of the identification information A in this case, too.

Furthermore, the magnetic field generating apparatus 20 may be provided with a communication function with an outside apparatus such as a workstation to input the identification information A via the communication function. That is, the outside apparatus functions as the input section 21. In this case, the magnetic field generating apparatus 20 need not be provided with the input section 21 such as a keypad, and it is possible to reduce the number of parts and thereby reduce the size of the magnetic field generating apparatus 20 and realize a cost reduction.

Modification Example of First Embodiment

Next, an in-vivo observation system 1A (see FIG. 3), which is an in-vivo information acquiring system according to a modification example of the first embodiment of the present invention, will be described. Since the in-vivo observation system 1A of the present modification example is similar to the in-vivo observation system 1 of the first embodiment, components having the same functions will be assigned the same reference numerals and descriptions thereof will be omitted.

In the in-vivo observation system 1 of the first embodiment, an activation instruction signal and a stop instruction signal for setting the in-vivo information acquiring section 13 of the capsule endoscope 10 in an operating state and a stopped state respectively are the same signal. By contrast, in the in-vivo observation system 1A according to the present modification example, an activation instruction signal and a stop instruction signal for setting the in-vivo information acquiring section 13 of a capsule endoscope 10A (see FIG. 3) generated by a magnetic field generating apparatus 20A (see FIG. 3) in an operating state and a stopped state respectively are different instruction signals.

The in-vivo observation system 1A uses different instruction signals for the activation instruction signal and the stop instruction signal, and can thereby define an instruction for setting an operating state or a stopped state and prevent erroneous activation/erroneous stopping of the capsule endoscope 10A.

Adopting a signal having a complicated bit pattern for the stop instruction signal in particular prevents the capsule endoscope 10A from stopping when an unintended AC magnetic field is received. Therefore, the in-vivo observation system 1 eliminates the possibility that the capsule endoscope 10A may be stopped by mistake during an inspection, and can thereby prevent a re-inspection caused by misoperation.

Furthermore, adopting a signal having a complicated bit pattern for the activation instruction signal eliminates the possibility that the capsule endoscope 10A may start operation when an unintended AC magnetic field is received and prevents operation from being started by mistake during transportation or the like and prevents power from being consumed.

Second Embodiment

Next, an in-vivo observation system 1B, which is an in-vivo information acquiring system according to a second embodiment of the present invention will be described. Since the in-vivo observation system 1B of the present embodiment is similar to the in-vivo observation system 1 of the first embodiment, components having the same functions will be assigned the same reference numerals and descriptions thereof will be omitted.

Figure 8:
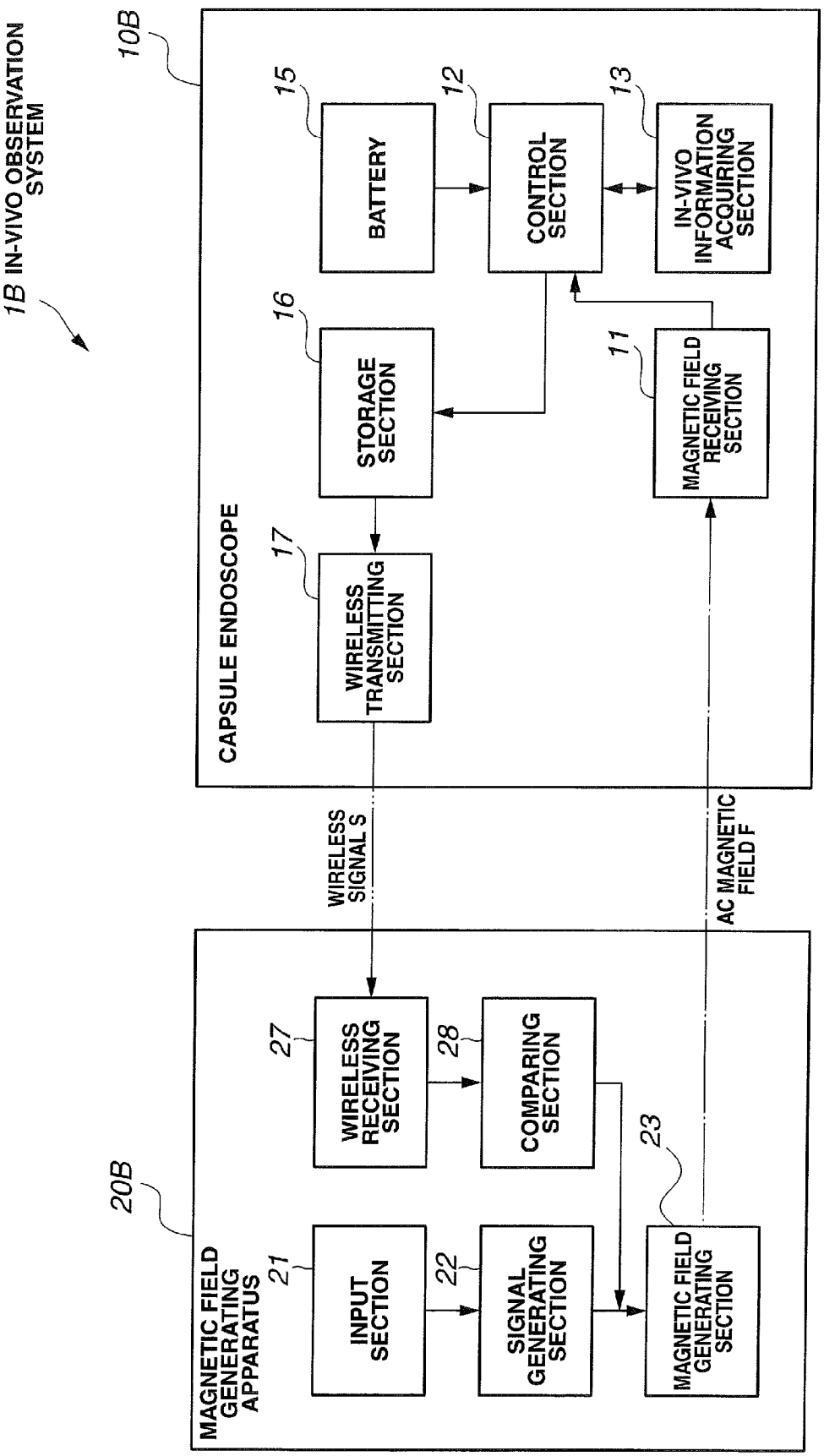
FIG. 8 is a block diagram illustrating a configuration of an in-vivo observation system according to a second embodiment.

FIG. 8 is a block diagram illustrating a configuration of the in-vivo observation system 1B of the second embodiment. As shown in FIG. 8, in the in-vivo observation system 1B, a capsule endoscope 10B and a magnetic field generating apparatus 20B exchange identification information using a wireless signal S in addition to an AC magnetic field signal F.

That is, the capsule endo scope 10B has a wireless transmitting section 17, which is a second wireless transmitting section that transmits the wireless signal S. The capsule endoscope 10B is not provided with the comparing section 14 provided in the capsule endoscope 10. The wireless transmitting section 17 is an identification information wireless transmitting section that wirelessly transmits identification information B and has a transmitting antenna and a transmitting circuit (not shown).

On the other hand, the magnetic field generating apparatus 20B has a wireless receiving section 27, which is a first wireless receiving section and a comparing section 28, which is a first comparing section. The wireless receiving section 27 is an identification information wireless receiving section having a receiving antenna (not shown) inside the signal generating section 22 and a receiving circuit, and receives the identification information B transmitted from the wireless transmitting section 17 of the capsule endoscope 10B. The comparing section 28 is, for example, an identification information comparing section inside the signal generating section 22. The comparing section 28 compares the identification information B received by the wireless receiving section 27 with identification information A inputted from an input section 21 and judges whether both pieces of information are the same or different.

Figure 9:
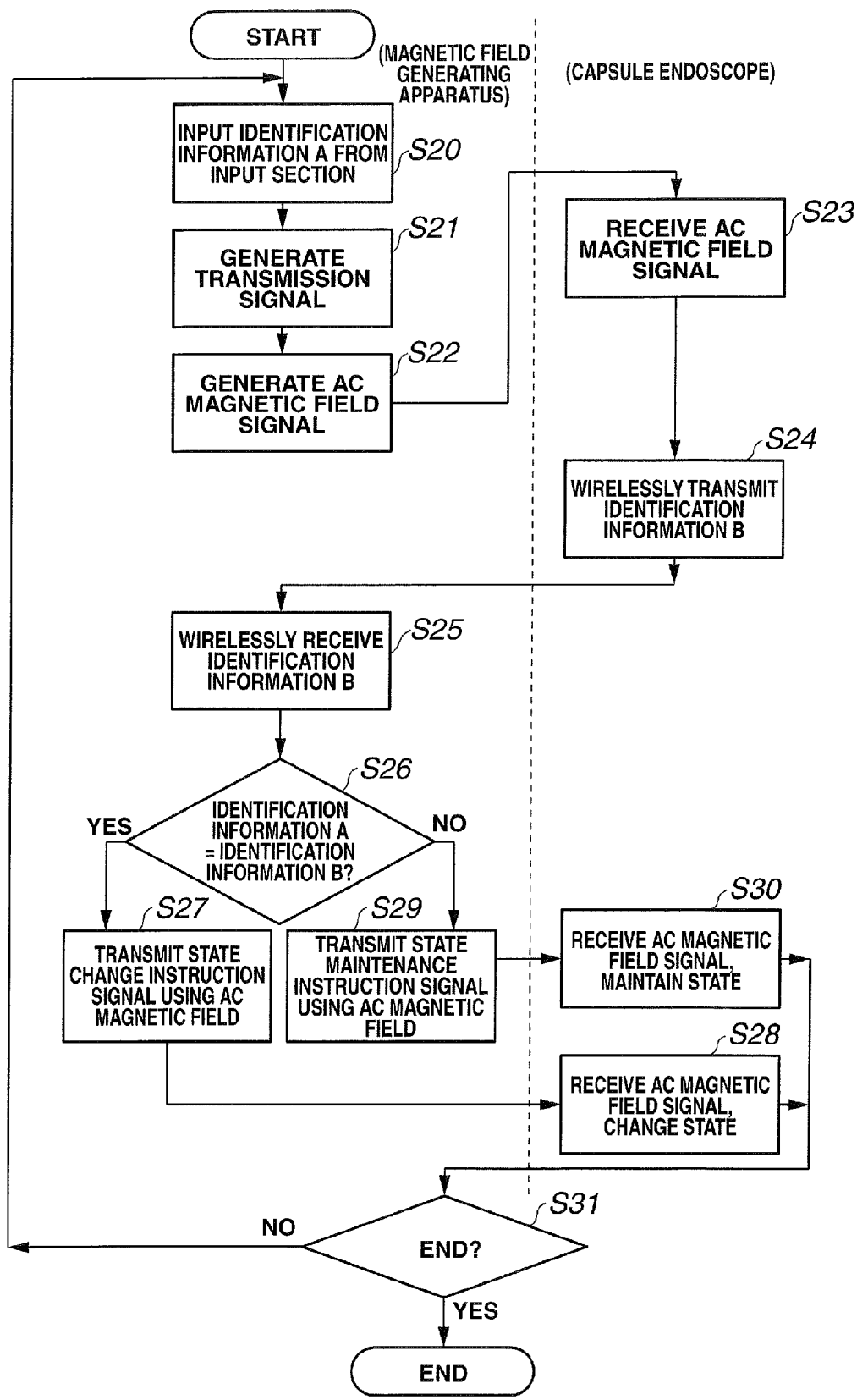
FIG. 9 is a flowchart illustrating a processing flow of the in-vivo observation system of the second embodiment.

Next, a processing flow of the in-vivo observation system 1B of the present embodiment will be described using FIG. 9. Hereinafter, the processing flow will be described using the flowchart in FIG. 9. The right side in FIG. 9 shows processing by the capsule endoscope 10B and the left side shows processing by the magnetic field generating apparatus 20B.

<Step S20> Input of Identification Information A

At the start, the in-vivo information acquiring section 13 of the capsule endoscope 10B is in a stopped state or an operating state. The user inputs the identification information A using the input section 21 of the magnetic field generating apparatus 20B.

<Step S21> Generation of Transmission Signal

The signal generating section 22 generates a signal to be transmitted to the driver 25 based on the inputted identification information A.

<Step S22> Generation of AC Magnetic Field Signal

The user operates the switch 24 of the magnetic field generating apparatus 20B to generate an AC magnetic field signal F made up of any one of an activation instruction signal for activating and a stop instruction signal for stopping the in-vivo information acquiring section 13 of the capsule endoscope 10B from the magnetic field generating section 23 and the identification information A.

<Step S23> Reception of AC Magnetic Field Signal

The magnetic field receiving section 11 of the capsule endoscope 10B receives the AC magnetic field F from the magnetic field generating apparatus 20B. That is, the magnetic field receiving section 11 converts the received AC magnetic field F to a DC current, and at the same time acquires the identification information A included in the AC magnetic field F.

<Step S24> Transmission of Identification Information B

The control section 12 of the capsule endoscope 10B reads the identification information B stored in the storage section 16 and transmits the identification information B from the wireless transmitting section 17 by means of a wireless signal.

<Step S25> Reception of Identification Information B

The wireless receiving section 27 of the magnetic field generating apparatus 20B receives the wireless signal S of the capsule endoscope 10B.

<Step S26> Judgment and Comparison of Identification Information

The comparing section 28 compares the received identification information B with the identification information A inputted from the input section 21 and judges whether both pieces of information are the same or different. The magnetic field generating apparatus 20B performs processing in S27 when the result of judgment by the comparing section 28 shows that both pieces of information are the same (Yes) and performs processing in S29 when both pieces of information are different (No).

<Step S27> Generation of AC Magnetic Field X

The magnetic field generating apparatus 20B generates an AC magnetic field X made up of an instruction signal for changing the potential of the gate of the power supply switch 18 of the capsule endoscope 10B.

<Step S28> Change of State (Toggle Operation)

Upon receiving the instruction signal for changing the potential of the gate of the power supply switch 18 from the magnetic field generating apparatus 20B, the control section 12 of the capsule endoscope 10B changes the potential of the gate of the power supply switch 18 and performs an inversion between a high impedance state and a conduction state. That is, when the power supply switch 18 is in a high impedance state, the control section 12 changes the state to a conduction state, and therefore the in-vivo information acquiring section 13 of the capsule endoscope 10B is placed in an operating state. On the other hand, when the power supply switch 18 is in a conduction state, the state is changed to a high impedance state and the in-vivo information acquiring section 13 of the capsule endoscope 10B is placed in a stopped state. That is, the power supply switch 18 performs a toggle operation.

<Step S29> Generation of AC Magnetic Field Y

The magnetic field generating apparatus 20B maintains the potential of the gate of the power supply switch 18 of the capsule endoscope 10B, that is, generates an AC magnetic field Y made up of a maintenance instruction signal for maintaining the power control state.

<Step S30> Maintenance of State

Upon receiving the maintenance instruction signal for maintaining the potential of the gate of the power supply switch 18 of the capsule endoscope 10B from the magnetic field generating apparatus 20B, the control section 12 of the capsule endo scope 10B does not change the potential of the gate of the power supply switch 18. Thus, the state of the in-vivo information acquiring section 13 of the capsule endoscope 10B, that is, the operating state or the stopped state is maintained.

<Step S31> Continuation of Processing

The in-vivo observation system 1B repeatedly performs the processing from step S20 until the user sends an end instruction.

As described above, the in-vivo observation system 1B of the present embodiment has the effect of the in-vivo observation system 1 of the first embodiment. Furthermore, since the in-vivo observation system 1B receives the identification information B from a predetermined capsule endoscope 10B to be controlled, the in-vivo observation system 1B can confirm whether or not the capsule endoscope 10B has successfully received the AC magnetic field. Therefore, the in-vivo observation system 1B can perform more reliable control than the in-vivo observation system 1 (1A). Furthermore, since the capsule endoscope 10B does not have the comparing section 14, the capsule endoscope 10B is smaller and achieves more power savings than the capsule endoscope 10 (10A).

In the case where the judgment result by the comparing section 28 shows that both pieces of information are different, the in-vivo observation system 1B may also adopt a specification that the magnetic field generating section 23 does not transmit any maintenance instruction signal, that is, no AC magnetic field is generated. In the case of such a specification, the capsule endoscope 10B maintains the state when it is not possible to receive any AC magnetic field made up of an instruction signal for a predetermined period after receiving the AC magnetic field signal for the first time. Here, the "predetermined period" may be a period exceeding a period necessary for the magnetic field generating section 23 to generate an AC magnetic field signal in the case where the judgment result by the comparing section 28 shows that both pieces of information are the same. Since the number of types of instruction signals becomes smaller, the in-vivo observation system can perform processing more easily.

The wireless transmitting section 17 may also serve as the wireless transmitting section 31, which is the video information wireless transmitting section of the in-vivo information acquiring section 13. Furthermore, the identification information B may also be added to or superimposed on the acquired in-vivo information and transmitted. The wireless transmitting section 17 in the above described configuration has a reduced number of parts, and can thereby realize downsizing of the capsule endoscope 10B and a cost reduction.

Furthermore, the identification information B transmitted from the wireless transmitting section 17 may be received using a receiver having a memory function for receiving an image shot by the capsule endoscope 10B and displayed on the display section thereof (not shown). Since the user also knows the operating state of the capsule endoscope 10B from the presence/absence of the displayed image simultaneously, the user can judge activation/stopping of the capsule endoscope 10B more reliably.

Furthermore, the magnetic field generating apparatus 20B may access the received identification information B from a workstation that displays the images shot by the capsule endoscope 10 through wired or wireless communication or a portable storage medium to manage the relationship between the acquired information and the identification information B.

Third Embodiment

Next, an in-vivo observation system 1C, which is an in-vivo information acquiring system according to a third embodiment of the present invention will be described. Since the in-vivo observation system 1C of the present embodiment is similar to the in-vivo observation system 1B of the second embodiment, components having the same functions will be assigned the same reference numerals and descriptions thereof will be omitted.

Figure 10:
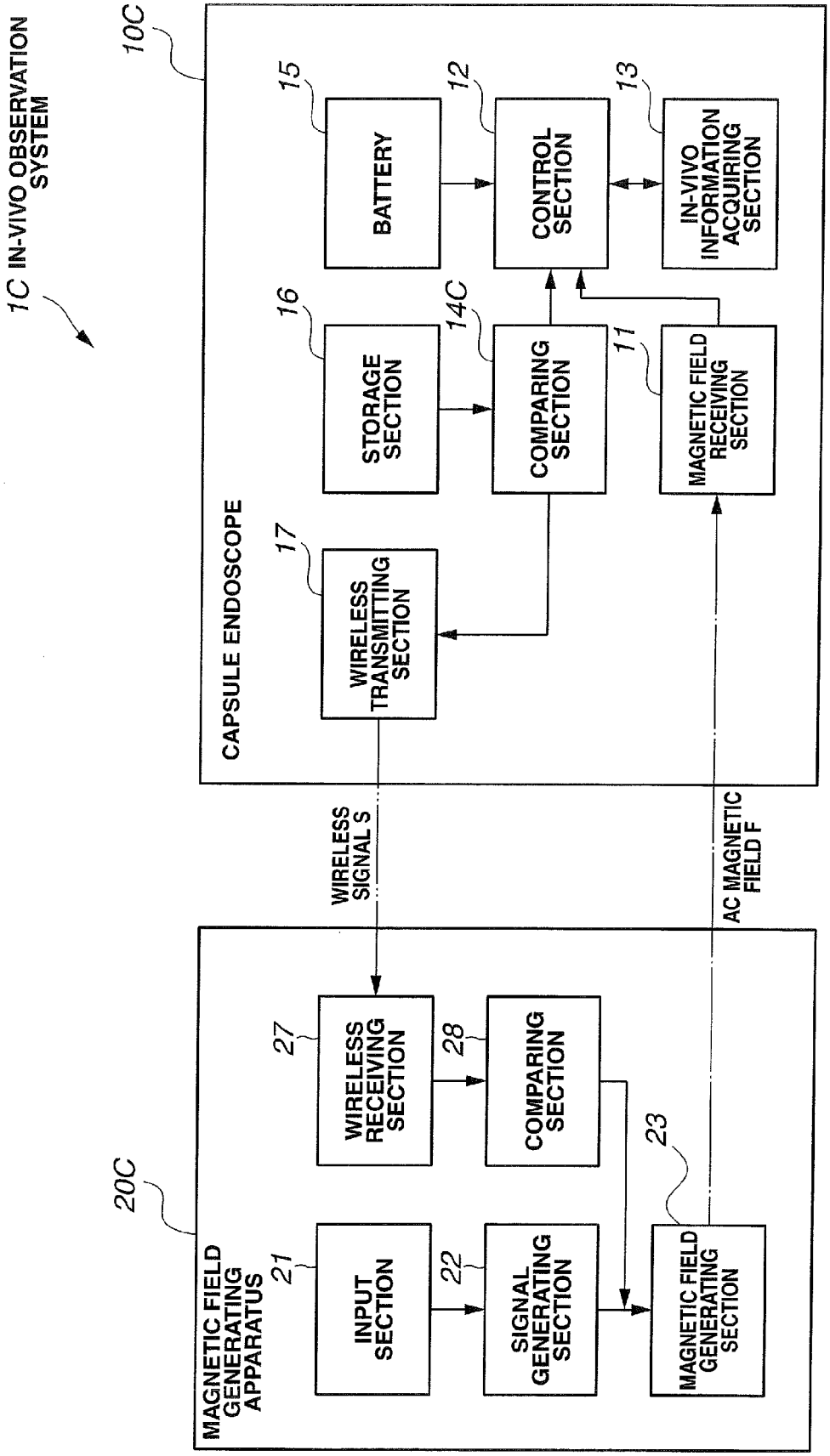
FIG. 10 is a block diagram illustrating a configuration of an in-vivo observation system according to a third embodiment.

FIG. 10 is a block diagram illustrating a configuration of the in-vivo observation system 1C of the third embodiment. As shown in FIG. 10, in the in-vivo observation system 1C, a capsule endoscope 10C and a magnetic field generating apparatus 20C perform handshake processing of exchanging identification information using a wireless signal S in addition to an AC magnetic field signal F, and especially comparing and judging received identification information.

The capsule endoscope 10C has the wireless transmitting section 17 and a comparing section 14C. On the other hand, the magnetic field generating apparatus 20C has the wireless receiving section 27 and the comparing section 28. That is, the capsule endoscope 10C and the magnetic field generating apparatus 20C have their respective comparing sections.

Figure 11:
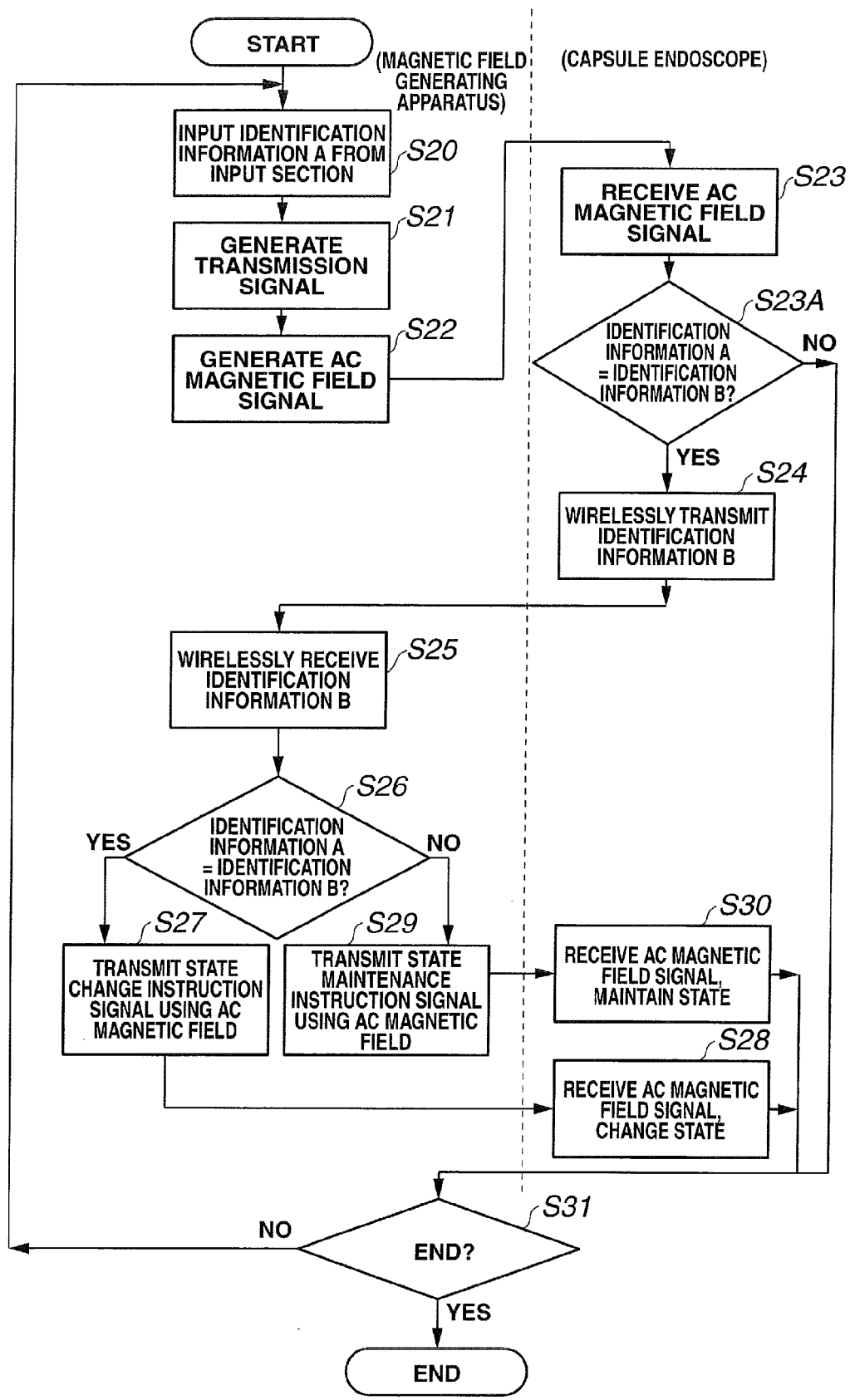
FIG. 11 is a flowchart illustrating a processing flow of the in-vivo observation system of the third embodiment.

Next, a processing flow of the in-vivo observation system 1C of the present embodiment will be described using FIG. 11. Hereinafter, the processing flow will be described using the flowchart in FIG. 11. The right side in FIG. 11 shows processing by the capsule endoscope 10C and the left side shows processing by the magnetic field generating apparatus 20C.

Hereinafter, only step S23A, which is different from the in-vivo observation system 1B of the second embodiment will be described.
<Step S23A> Comparison and Judgment of Identification Information The comparing section 14C of the capsule endoscope 10C makes a comparison and judges whether the received identification information A is equal to the identification information B stored in the storage section 16. The capsule endoscope 10C performs the processing in S24 when the judgment result of the comparing section 14C shows that both pieces of information are the same (Yes) and performs the processing in S31 when both pieces of information are different (No).

That is, in the in-vivo observation system 1C, the identification information is compared and judged by both the comparing section 14C of the capsule endoscope 10C and the comparing section 28 of the magnetic field generating apparatus 20C. Therefore, the in-vivo observation system 1C has the effect of the in-vivo observation system 1 of the first embodiment, and is more resistant to misoperations.

Fourth Embodiment

Next, an in-vivo observation system 1D, which is an in-vivo information acquiring system according to a fourth embodiment of the present invention will be described. Since the in-vivo observation system 1D of the present embodiment is similar to the in-vivo observation system 1C of the third embodiment, components having the same functions will be assigned the same reference numerals and descriptions thereof will be omitted.

Figure 12:
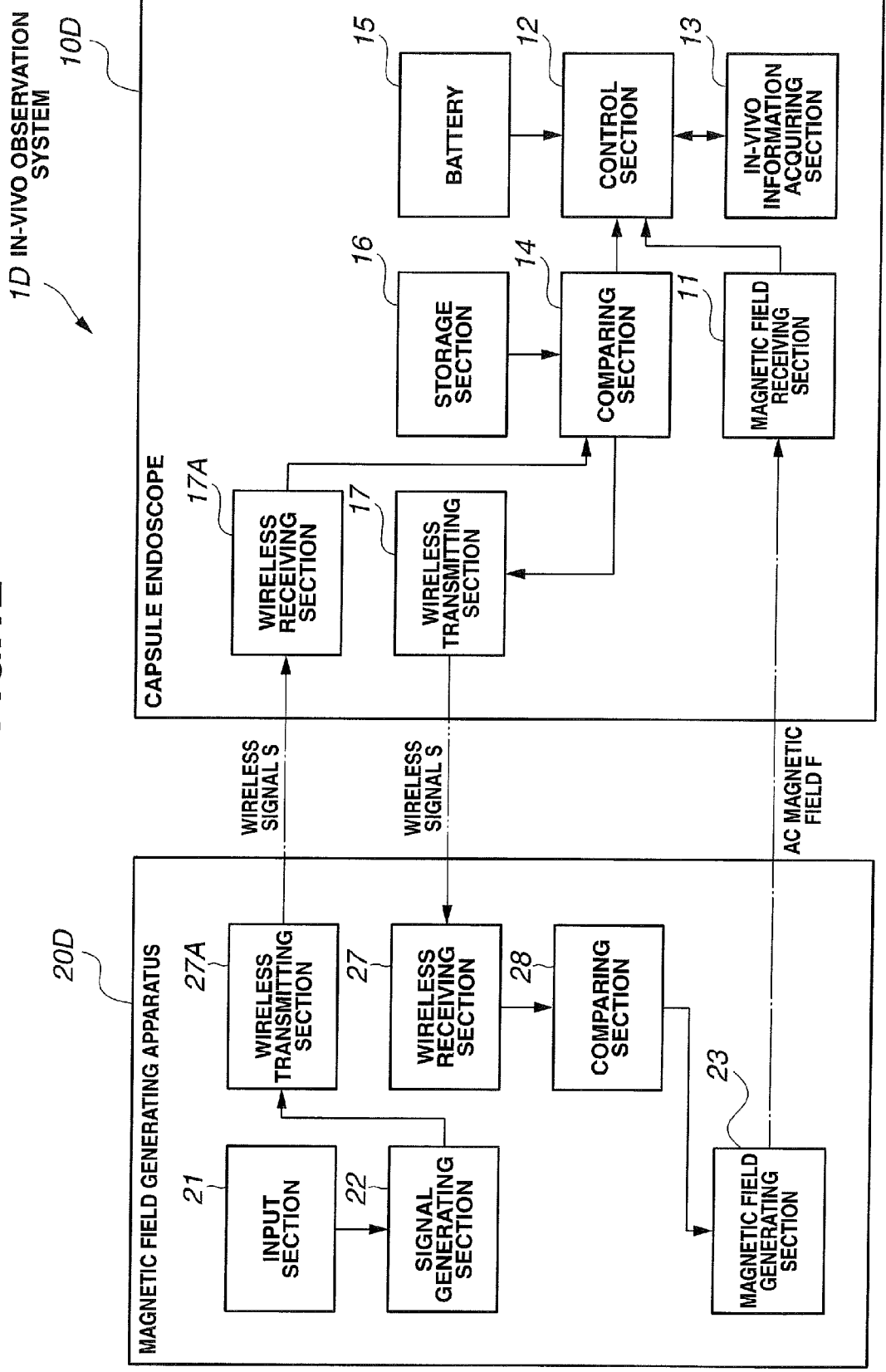
FIG. 12 is a block diagram illustrating a configuration of an in-vivo observation system according to a fourth embodiment.

FIG. 12 is a block diagram illustrating a configuration of the in-vivo observation system 1D of the fourth embodiment. As shown in FIG. 12, in the in-vivo observation system 1D, a capsule endoscope 10D and a magnetic field generating apparatus 20D have the wireless transmitting section 17, which is a second wireless transmitting section, or a wireless transmitting section 27A, which is a first wireless transmitting section, and a wireless receiving section 17A, which is a second wireless receiving section, or the wireless receiving section 27, which is a first wireless receiving section.

The wireless transmitting section 17 transmits identification information B and the wireless receiving section 17A receives identification information A. On the other hand, the wireless transmitting section 27A transmits the identification information A and the wireless receiving section 27 receives the identification information B.

In the in-vivo observation system 1D, the wireless transmitting section 27A of the magnetic field generating apparatus 20D wirelessly transmits the identification information A instead of a magnetic field signal and the wireless receiving section 17A of the capsule endoscope 10D receives the identification information A.

The in-vivo observation system 1D has the effect of the in-vivo observation system 1C and can use a simple signal for the AC magnetic field generated to wirelessly transmit the identification information A. Furthermore, the in-vivo observation system 1D can easily transmit a complicated signal as the identification information A, and is therefore more resistant to misoperations.

Fifth Embodiment

Next, an in-vivo observation system 1E, which is an in-vivo information acquiring system according to a fifth embodiment of the present invention will be described. Since the in-vivo observation system 1E of the present embodiment is similar to the in-vivo observation system 1D of the fourth embodiment, components having the same functions will be assigned the same reference numerals and descriptions thereof will be omitted.

Figure 13:
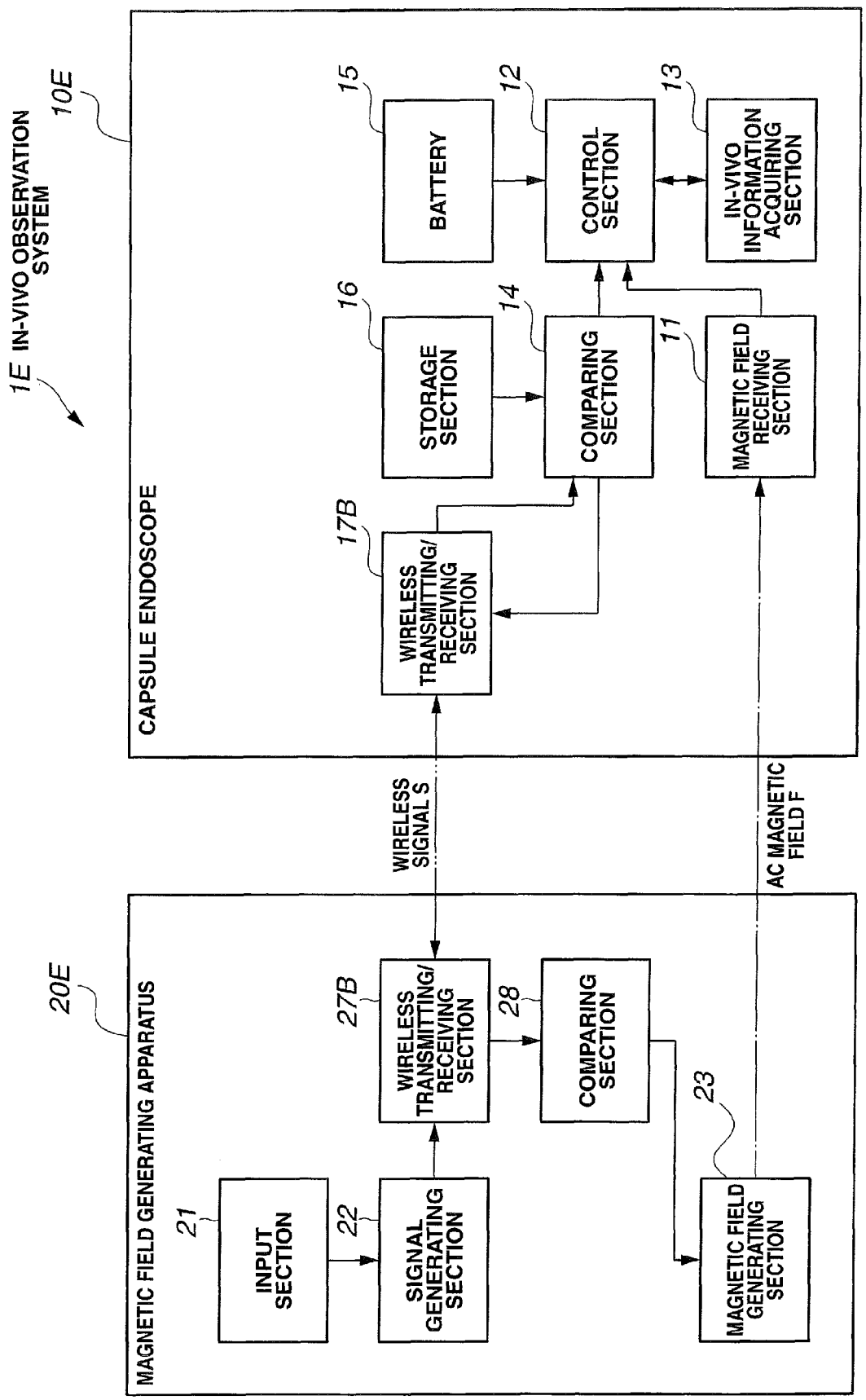
FIG. 13 is a block diagram illustrating a configuration of an in-vivo observation system according to a fifth embodiment.

FIG. 13 is a block diagram illustrating a configuration of the in-vivo observation system 1E of the fifth embodiment. As shown in FIG. 13, in the in-vivo observation system 1E, a capsule endoscope 10E and a magnetic field generating apparatus 20E have a wireless transmitting/receiving section 17B, which is a second wireless transmitting/receiving section or a wireless transmitting/receiving section 27B, which is a first wireless transmitting/receiving section.

The wireless transmitting/receiving section 17B transmits identification information B and receives identification information A. On the other hand, the wireless transmitting/receiving section 27B transmits the identification information A and receives the identification information B.

The wireless transmitting/receiving section 17B of the capsule endoscope 10E may also serve as a video information wireless transmitting/receiving section (not shown) or the like of the in-vivo information acquiring section 13 and the wireless transmitting/receiving section 27B of the magnetic field generating apparatus 20E may also serve as a video information wireless transmitting/receiving section (not shown) of a receiver (not shown) for transmitting/receiving a signal to/from the video information wireless transmitting/receiving section of the capsule endoscope 10C.

The in-vivo observation system 1E of the present embodiment has the same effect as that of the in-vivo observation system 1D of the fourth embodiment and since the wireless transmitting/receiving section has the functions of the wireless transmitting section and the wireless receiving section, fewer components are required.

Although information specific to a specific capsule endoscope to be controlled is used as identification information in the descriptions above, information of the examinee, for example, feature information of the examinee's face or the like may be used as the identification information. In this case, the examinee's face may be photographed beforehand, the feature data may be stored in the storage section of the capsule endoscope as appropriate using a publicly known feature extracting technique. The capsule endoscope is taken out of the package, set in an activated state and the examinee's face is photographed using the image pickup section of the capsule endoscope. That is, the examinee's face is photographed before shooting an image of the interior of the body of the examinee. The input section of the magnetic field generating apparatus acquires the image from the reception apparatus which has received the image of the examinee's face photographed by the capsule endoscope and obtains feature data using a publicly known feature extracting technique. The comparing section of the magnetic field generating apparatus compares the feature data of the examinee stored in the storage section of the capsule endoscope with the feature data of the examinee photographed by the capsule endoscope and judges whether or not both pieces of data match.

Furthermore, although a case has been described above where the capsule endoscope is taken as an example of the in-vivo information acquiring apparatus, the in-vivo information acquiring system of the present invention is also applicable to various types of capsule in-vivo observation apparatus such as a capsule medical apparatus for collecting digestive juices, swallow capsule pH sensor or capsule temperature sensor.

Finally, diagnosis or observation using a capsule endoscope that controls activation/stopping of a power supply to the main function sections under the control of an AC magnetic field will be described briefly.

First, the user takes the capsule endoscope accommodated in the accommodation case out of the case.

The user applies an AC magnetic field to the capsule endoscope taken out of the case, activates the main function sections of the capsule endoscope and checks the operation. The user administers the capsule endoscope to the examinee, instructs the examinee to swallow the capsule endoscope and starts an observation or a diagnosis. The user may also apply an AC magnetic field with the capsule endoscope accommodated in the accommodation case, activate the capsule endoscope and then take the capsule endoscope out of the accommodation case and administer the capsule endoscope to the examinee.

Once the observation or the diagnosis is started, the user may activate the capsule endoscope as is or may freely control activation/stopping of the capsule endoscope by applying an AC magnetic field from outside. For example, for a period during which the capsule endoscope is passing through a region where no observation is necessary, the user may stop operation of the capsule endoscope and activate the capsule endoscope when the capsule endoscope reaches a desired region by applying an AC magnetic field from outside and carry out an observation or a diagnosis.

Thus, for the period during which the capsule endoscope is passing through a region where no observation is necessary, the user stops the operation of the capsule endoscope and activates the capsule endoscope when the capsule endoscope reaches a desired region, and can thereby prevent battery consumption, reliably perform an observation or a diagnosis of the desired region, and diagnostic performance can thereby be expected to improve. That is, according to the present embodiment, it is possible to easily and freely control activation and stopping of the capsule endoscope and prevent battery consumption, and diagnostic performance can thereby be expected to improve.

In the present embodiment, it is not impossible to use a DC magnetic field as the outside magnetic field. However, a reed switch widely used to detect a DC magnetic field often requires anti-chattering measures and thereby requires the transmission rate of information to be reduced. When the transmission rate decreases, information transmission takes more time, the position/orientation of the capsule endoscope may change in the body in the meantime, an error may occur in control of ON/OFF of contact of the reed switch. Furthermore, when information is transmitted, since the reed switch is recovered by ON/OFF of the contact, only binary information can be sent. Furthermore, since the reed switch has low sensitivity of magnetic field detection, it is necessary to generate a strong magnetic field to send an activation/stopping instruction from outside the body when the capsule endoscope is swallowed, which requires a large magnetic field generating apparatus and great electric power. For this reason, when a DC magnetic field is used as the outside magnetic field, it is preferable to use an MR element, a GMR element, an MI element or an FG element or the like, which has higher sensitivity and is capable of demodulating information with two or more values rather than the reed switch as the magnetic field detection element.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An in-vivo information acquiring system comprising:
a magnetic field generating apparatus comprising
an input section for inputting first identification information that allows an in-vivo information acquiring apparatus to be controlled to be distinguished from other in-vivo information acquiring apparatuses, and
a magnetic field generating section that generates a magnetic field signal that controls the in-vivo information acquiring apparatus to be controlled; and
an in-vivo information acquiring apparatus introduced into an object to be examined and to be controlled, comprising
an in-vivo information acquiring section that acquires information inside the object to be examined,
a power supply source that supplies power to be used to drive the in-vivo information acquiring section,
a magnetic field signal receiving section disposed outside that receives the magnetic field signal from the magnetic field generating apparatus,
a storage section that stores second identification information that allows the in-vivo information acquiring apparatus to be controlled to be distinguished from the other in-vivo information acquiring apparatuses, and a power supply control section that controls a power supply from the power supply source to the in-vivo information acquiring section, wherein when the in-vivo information acquiring system has any one of configurations where (1) the magnetic field generating apparatus comprises a first comparing section that compares the first identification information with the second identification information and judges whether both pieces of information are the same or different, and (2) the magnetic field generating apparatus comprises the first comparing section and the in-vivo information acquiring apparatus to be controlled comprises the second comparing section which compares the first identification information with the second identification information and judges whether both pieces of information are the same or different, and when the judgment of the first comparing section is a judgment that both pieces of information are the same, the power supply control section supplies or shuts off power from the power supply source to the in-vivo information acquiring section.

2. The in-vivo information acquiring system according to claim 1, wherein the first comparing section compares the first identification information inputted from the input section with the second identification information received from the in-vivo information acquiring apparatus to be controlled and judges whether both pieces of information are the same or different, and when the judgment by the first comparing section shows that both pieces of information are the same, the magnetic field generating section generates a magnetic field signal of an instruction signal for the power supply control section.

3. The in-vivo information acquiring system according to claim 2, wherein the instruction signal is any one of an activation instruction signal for the power supply control section to perform control so as to supply the power from the power supply source to the in-vivo information acquiring section, a stop instruction signal to perform control so as to shut off the power from the power supply source to the in-vivo information acquiring section and a maintenance instruction signal for maintaining a control state of the power from the power supply source to the in-vivo information acquiring section.

4. The in-vivo information acquiring system according to claim 1, wherein the in-vivo information acquiring apparatus to be controlled comprises a second comparing section, the second comparing section compares the second identification information stored in the storage section with the first identification information received from the in-vivo information acquiring apparatus to be controlled and judges whether both pieces of information are the same or different, and when the judgment by the second comparing section shows that both pieces of information are the same, the second identification information is transmitted, the magnetic field generating apparatus comprises the first comparing section, the first comparing section compares the first identification information inputted from the input section with the second identification information received from the in-vivo information acquiring apparatus to be controlled and judges whether both pieces of information are the same or different, and when the judgment by the first comparing section shows that both pieces of information are the same, the magnetic field generating section generates a magnetic field signal of an instruction signal for the power supply control section.

5. The in-vivo information acquiring system according to claim 4, wherein the magnetic field generating apparatus comprises a first wireless receiving section that wirelessly receives the second identification information, and the in-vivo information acquiring apparatus to be controlled comprises a second wireless transmitting section that wirelessly transmits the second identification information.

6. The in-vivo information acquiring system according to claim 4, wherein the magnetic field generating apparatus comprises a first wireless transmitting section that wirelessly transmits the first identification information and a first wireless receiving section that wirelessly receives the second identification information, and the in-vivo information acquiring apparatus to be controlled comprises a second wireless transmitting section that wirelessly transmits the second identification information and a second wireless receiving section that wirelessly receives the first identification information.

7. The in-vivo information acquiring system according to claim 4, wherein the magnetic field generating apparatus comprises a first wireless transmitting/receiving section that wirelessly transmits the first identification information and wirelessly receives the second identification information, and the in-vivo information acquiring apparatus to be controlled comprises a second wireless transmitting/receiving section that wirelessly transmits the second identification information and wirelessly receives the first identification information.

8. The in-vivo information acquiring system according to claim 4, wherein the magnetic field generating section generates a magnetic field signal of an instruction signal for the power supply control section and a magnetic field signal of the first identification information.

9. The in-vivo information acquiring system according to claim 8, wherein the magnetic field signal generating section generates a magnetic field signal of the instruction signal and a magnetic field signal of the first identification information in time sequence.

10. The in-vivo information acquiring system according to claim 8, wherein the magnetic field signal generating section generates a magnetic field signal which is the instruction signal superimposed on the first identification information.

11. The in-vivo information acquiring system according to claim 1, wherein the magnetic field signal generated by the magnetic field signal generating section is an AC magnetic field signal.

12. The in-vivo information acquiring system according to claim 11, wherein the in-vivo information acquiring apparatus to be controlled is a capsule endoscope.

13. A method for controlling an in-vivo information acquiring system comprising:

a first identification information inputting step of inputting first identification information that allows an in-vivo information acquiring apparatus to be controlled to be distinguished from other in-vivo information acquiring apparatuses from an input section of a magnetic field generating apparatus that generates a magnetic field signal for controlling the in-vivo information acquiring apparatus to be controlled and is disposed outside the in-vivo information acquiring apparatus to be controlled;

an identification information magnetic field generating step of generating a magnetic field signal of the first identification information from a magnetic field generating section of the magnetic field generating apparatus;

a magnetic field signal receiving step of a magnetic field signal receiving section of the in-vivo information acquiring apparatus to be controlled receiving a magnetic field signal of the first identification information from the magnetic field generating apparatus;

a second identification information transmitting step of a wireless transmitting section of the in-vivo information acquiring apparatus to be controlled wirelessly transmitting second identification information stored in a storage section of the in-vivo information acquiring apparatus to be controlled that allows the in-vivo information acquiring apparatus to be controlled to be distinguished from other in-vivo information acquiring apparatuses;

a second identification information receiving step of a wireless receiving section of the magnetic field generating apparatus receiving second identification information from the in-vivo information acquiring apparatus to be controlled;

a comparing step of a comparing section of the magnetic field generating apparatus comparing the first identification information inputted in the first identification information inputting step with the second identification information received in the second identification information receiving step and judging whether both pieces of information are the same or different;

an instruction magnetic field signal transmitting step of transmitting a magnetic field signal of an instruction signal for the in-vivo information acquiring apparatus to be controlled from the magnetic field generating section based on the judgment by the comparing section;

a magnetic field signal receiving step of a magnetic field signal receiving section of the in-vivo information acquiring apparatus to be controlled receiving the magnetic field signal of the instruction signal from the magnetic field generating apparatus; and a power supply controlling step of a power supply control section controlling whether power from a power supply source to an in-vivo information acquiring section is supplied or shut off based on the instruction signal.

14. The method for controlling an in-vivo information acquiring system according to claim 13, further comprising a second comparing step of a second comparing section of the in-vivo information acquiring apparatus to be controlled comparing the first identification information received from the magnetic field generating apparatus with the second identification information stored in the storage section and judging whether both pieces of information are the same or different, wherein in the second identification information transmitting step, when the judgment by the second comparing section is a judgment that both pieces of information are the same, a wireless transmitting section of the in-vivo information acquiring apparatus to be controlled wirelessly transmits the second identification information.

15. The method for controlling an in-vivo information acquiring system according to claim 14, wherein the instruction signal is any one of an activation instruction signal for the power supply control section to perform control so as to supply the power from the power supply source to the in-vivo information acquiring section, a stop instruction signal to perform control so as to shut off the power from the power supply source to the in-vivo information acquiring section and a maintenance instruction signal for maintaining a control state of the power from the power supply source to the in-vivo information acquiring section.

16. The method for controlling an in-vivo information acquiring system according to claim 15, wherein the magnetic field signal generated by the magnetic field signal generating section is an AC magnetic field signal, and the in-vivo information acquiring apparatus to be controlled is a capsule endoscope.

\* \* \* \* \*